(12) United States Patent
Elashvili

(10) Patent No.: US 7,470,520 B1
(45) Date of Patent: Dec. 30, 2008

(54) **METHOD FOR *ENTEROBACTER* IDENTIFICATION**

(75) Inventor: Ilya Elashvili, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 217 days.

(21) Appl. No.: 11/272,416

(22) Filed: Nov. 9, 2005

(51) Int. Cl.
*C12Q 1/10* (2006.01)

(52) U.S. Cl. .................... 435/38; 435/4; 435/34

(58) Field of Classification Search ............ None
See application file for complete search history.

(56) References Cited

OTHER PUBLICATIONS

Ohkusu, Kiyofumi "Cost-Effective and Rapid Presumptive Identification of Gram-Negative Bacilli in Routine Urine, Pus, and Stool Cultures: Evaluation of the Use of CHROMagar Orientation Medium in Conjuction with Simple Biochemical Tests," (J. Clin. Microbiol.) Dec. 2000, vol. 38, No. 12, p. 4586-4592.*

Merlino et al, "Evaluation of CHROMagar Prientation for Differentiation and Presumptive Identification of Gram-Negative Bacilli and Enterococcus Species," (J. Clin. Microbiol.), Jul. 1996, vol. 34, No. 7, p. 1788-1793.*

Nord et al, "Four Hour-Tests for the Identification of Enterobacteriaceae," (Med. Microbiol. Immunol.), 1975, vol. 161, p. 231-238.*

* cited by examiner

*Primary Examiner*—Cecilia Tsang
*Assistant Examiner*—Amanda P Wood
(74) *Attorney, Agent, or Firm*—Ulysses John Biffoni

(57) ABSTRACT

The present invention is generally related to products and methods permitting the identification of *Enterobacter* species organisms. In addition, the invention provides the capability to differentiate *Enterobacter* infections from other acute bacterial infections.

6 Claims, 8 Drawing Sheets

**General Characteristics of *Enterobacter* spp.**

| XLD | Mucoid yellow colonies w/o black centers |
|---|---|
| CHRO | Metallic medium to dark blue or purple-blue colonies |
| TSI | All with acid butt and most slants with acid butt and gas bubbles. None produce $H_2S$ (i.e., no black color) |
| VP | Positive (see FIG. 2) |
| Mot | Motile (see FIG. 2) |
| LDC | Negative (see FIG. 2) |
| ODC | Positive (see FIG. 2) |
| IND | Negative (see FIG. 2) |
| CIT | Positive (see FIG. 2) |

FIG. 1

Title of the Invention: Method of Enterobacter Identification
Inventor's Name: Ilya Elashvili
Docket Number: DAM 610-04

Prior Art

Characteristics of *Klebsiella*, *Citrobacter*, and *Enterobacter* Species*

| | VP | MO | LDC | ODC | IND | CIT | H$_2$S | YP |
|---|---|---|---|---|---|---|---|---|
| Klebsiella | | | | | | | | |
| K. pneumoniae' | 98 | 0 | 98 | 0 | 0 | 98 | 0 | 0 |
| K. oxytoca' | 95 | 0 | 99 | 0 | 99 | 95 | 0 | 1 |
| K. ornithinolytica' | 70 | 0 | 100 | 100 | 100 | 100 | 0 | 0 |
| K. planticola' | 98 | 0 | 100 | 0 | 20 | 100 | 0 | 1 |
| K. ozaenae' | 0 | 0 | 40 | 3 | 0 | 30 | 0 | 0 |
| K. rhinoscleromatis' | 0 | 0 | 0 | 0 | 0 | 0 | 0 | 0 |
| K. terrigena | 100 | 0 | 100 | 20 | 0 | 40 | 0 | 0 |
| Citrobacter | | | | | | | | |
| C. freundii' | 0 | 89 | 0 | 0 | 33 | 78 | 78 | 0 |
| C. diversus (koseri)' | 0 | 95 | 0 | 99 | 99 | 99 | 0 | 0 |
| C. amalonaticus' | 0 | 95 | 0 | 95 | 100 | 95 | 5 | 0 |
| C. farmeri' | 0 | 97 | 0 | 100 | 100 | 10 | 0 | 0 |
| C. youngae' | 0 | 95 | 0 | 5 | 15 | 75 | 65 | 0 |
| C. braakii' | 0 | 87 | 0 | 93 | 33 | 87 | 80 | 0 |
| C. werkmanii' | 0 | 100 | 0 | 0 | 0 | 100 | 100 | 0 |
| C. sedlakii' | 0 | 100 | 0 | 100 | 83 | 83 | 0 | 0 |
| Citrobacter sp. 9' | 0 | 0 | 0 | 100 | 0 | 0 | 0 | 0 |
| Citrobacter sp. 10' | 0 | 67 | 0 | 0 | 0 | 33 | 67 | 0 |
| Citrobacter sp. 11' | 0 | 100 | 0 | 0 | 100 | 100 | 67 | 0 |
| Enterobacter | | | | | | | | |
| E. aerogenes' | 98 | 97 | 98 | 98 | 0 | 95 | 0 | 0 |
| E. cloacae' | 100 | 95 | 0 | 96 | 0 | 100 | 0 | 0 |
| E. agglomerans group' | 70 | 85 | 0 | 0 | 20 | 50 | 0 | 75 |
| E. gergoviae' | 100 | 90 | 90 | 100 | 0 | 99 | 0 | 0 |
| E. sakazakii' | 100 | 96 | 0 | 91 | 11 | 99 | 0 | 98 |
| E. taylorae' | 100 | 99 | 0 | 99 | 0 | 100 | 0 | 0 |
| E. amnigenus biogroup 1' | 100 | 92 | 0 | 55 | 0 | 70 | 0 | 0 |
| E. amnigenus biogroup 2' | 100 | 100 | 0 | 100 | 0 | 100 | 0 | 0 |
| E. asburiae' | 2 | 0 | 0 | 95 | 0 | 100 | 0 | 0 |
| E. hormaechei' | 100 | 52 | 0 | 91 | 0 | 96 | 0 | 0 |
| E. intermedium | 100 | 89 | 0 | 89 | 0 | 65 | 0 | 0 |
| E. cancerogenus | 100 | 100 | 0 | 100 | 0 | 100 | 0 | 0 |
| E. dissolvens | 100 | 0 | 0 | 100 | 0 | 100 | 0 | 0 |
| E. nimipressuralis | 100 | 0 | 0 | 100 | 0 | 0 | 0 | 0 |

*Each number gives the percentage of positive reactions after 2 days of incubation at 36°C (17.3).
VP=Voges-Proskauer, LDC=lysine decarboxylase, ODC=ornithine decarboxylase, YP=yellow pigment
' Known to occur in clinical specimens.

FIG.2

Strain Distribution (%) of H₂S-negative Species into Four Groups after the Initial Screening

|  | Group 1 | Group 2 | Group 3 | Group 4 |
|---|---|---|---|---|
| *Klebsiella* | VP⁻ Mot⁻ | VP⁻ Mot⁺ | VP⁺ Mot⁻ | VP⁺ Mot⁺ |
| K. pneumoniae' | 2 | 0 | 98 | 0 |
| K. oxytoca' | 5 | 0 | 95 | 0 |
| K. ornithinolytica' | 30 | 0 | 70 | 0 |
| K. planticola' | 2 | 0 | 98 | 0 |
| K. ozaenae' | 100 | 0 | 0 | 0 |
| K. rhinoscleromatis' | 100 | 0 | 0 | 0 |
| K. terrigena | 0 | 0 | 100 | 0 |
|  |  |  |  |  |
| *Citrobacter* |  |  |  |  |
| C. freundii' | 2.42 | 19.58 | 0 | 0 |
| C. diversus (koseri)' | 5 | 95 | 0 | 0 |
| C. amalonaticus' | 4.75 | 90.25 | 0 | 0 |
| C. farmeri' | 3 | 97 | 0 | 0 |
| C. youngae' | 1.75 | 33.25 | 0 | 0 |
| C. braakii' | 5.2 | 34.8 | 0 | 0 |
| C. werkmanii' | 0 | 0 | 0 | 0 |
| C. sedlakii' | 0 | 100 | 0 | 0 |
| Citrobacter sp. 9' | 100 | 0 | 0 | 0 |
| Citrobacter sp. 10' | 10.89 | 22.11 | 0 | 0 |
| Citrobacter sp. 11' | 0 | 33 | 0 | 0 |
|  |  |  |  |  |
| *Enterobacter* |  |  |  |  |
| E. aerogenes' | 0.06 | 1.94 | 2.94 | 95.06 |
| E. cloacae' | 0 | 0 | 5 | 95 |
| E. agglomerans group' | 4.5 | 25.5 | 10.5 | 59.5 |
| E. gergoviae' | 0 | 0 | 10 | 90 |
| E. sakazakii' | 0 | 0 | 4 | 96 |
| E. taylorae' | 0 | 0 | 1 | 99 |
| E. amnigenus biogroup 1' | 0 | 0 | 8 | 92 |
| E. amnigenus biogroup 2' | 0 | 0 | 0 | 100 |
| E. asburiae' | 98 | 0 | 2 | 0 |
| E. hormaechei' | 0 | 0 | 48 | 52 |
| E. intermedium | 0 | 0 | 11 | 89 |
| E. cancerogenus | 0 | 0 | 0 | 100 |
| E. dissolvens | 0 | 0 | 100 | 0 |
| E. nimipressuralis | 0 | 0 | 100 | 0 |

FIG. 3

Distribution Percentages of Positive-Test Phenotype Strains

| Group 1 | VP | Motility | LDC | ODC | Indole | Citrate | H$_2$S | YP | adonitol |
|---|---|---|---|---|---|---|---|---|---|
| K. ornithinolytica' | 70 | 0 | 100 | 100 | 100 | 100 | 0 | 0 | 100 |
| K. ozaenae' | 0 | 0 | 40 | 3 | 0 | 30 | 0 | 0 | 97 |
| K. rhinoscleromatis' | 0 | 0 | 0 | 0 | 0 | 0 | 0 | 0 | 100 |
| Citrobacter sp. 9' | 0 | 0 | 0 | 100 | 0 | 0 | 0 | 0 | 0 |
| Citrobacter sp. 10' | 0 | 67 | 0 | 0 | 0 | 33 | 67 | 0 | 0 |
| E. aerogenes' | 98 | 97 | 98 | 98 | 0 | 95 | 0 | 0 | 98 |
| E. agglomerans group' | 70 | 85 | 0 | 0 | 20 | 50 | 0 | 75 | 7 |
| E. asburiae' | 2 | 0 | 0 | 95 | 0 | 100 | 0 | 0 | 0 |

| Group 2 | VP | Motility | LDC | ADH | ODC | Indole | Citrate | H2S | YP |
|---|---|---|---|---|---|---|---|---|---|
| C. freundii' | 0 | 89 | 0 | 67 | 0 | 33 | 78 | 78 | 0 |
| C. diversus (koseri)' | 0 | 95 | 0 | 80 | 99 | 99 | 99 | 0 | 0 |
| C. amalonaticus' | 0 | 95 | 0 | 85 | 95 | 100 | 95 | 5 | 0 |
| C. farmeri' | 0 | 97 | 0 | 85 | 100 | 100 | 10 | 0 | 0 |
| C. youngae' | 0 | 95 | 0 | 50 | 5 | 15 | 75 | 65 | 0 |
| C. braakii' | 0 | 87 | 0 | 67 | 93 | 33 | 87 | 60 | 0 |
| C. sedlakii' | 0 | 100 | 0 | 100 | 100 | 83 | 83 | 0 | 0 |
| Citrobacter sp. 10' | 0 | 67 | 0 | 33 | 0 | 0 | 33 | 67 | 0 |
| Citrobacter sp. 11' | 0 | 100 | 0 | 67 | 0 | 100 | 100 | 67 | 0 |
| E. aerogenes' | 98 | 97 | 98 | 0 | 98 | 0 | 95 | 0 | 0 |
| E. agglomerans group' | 70 | 85 | 0 | 0 | 0 | 20 | 50 | 0 | 75 |

| Group 3 | VP | Motility | LDC | ODC | Indole | Citrate | H2S | YP |
|---|---|---|---|---|---|---|---|---|
| K. pneumoniae' | 98 | 0 | 98 | 0 | 0 | 98 | 0 | 0 |
| K. oxytoca' | 95 | 0 | 99 | 0 | 99 | 95 | 0 | 1 |
| K. ornithinolytica' | 70 | 0 | 100 | 100 | 100 | 100 | 0 | 0 |
| K. planticola' | 98 | 0 | 100 | 0 | 20 | 100 | 0 | 1 |
| K. terrigena | 100 | 0 | 100 | 20 | 0 | 40 | 0 | 0 |
| E. aerogenes' | 98 | 97 | 98 | 98 | 0 | 95 | 0 | 0 |
| E. cloacae' | 100 | 95 | 0 | 96 | 0 | 100 | 0 | 0 |
| E. agglomerans group' | 70 | 85 | 0 | 0 | 20 | 50 | 0 | 75 |
| E. gergoviae' | 100 | 90 | 90 | 100 | 0 | 99 | 0 | 0 |
| E. sakazakii' | 100 | 96 | 0 | 91 | 11 | 99 | 0 | 98 |
| E. taylorae' | 100 | 99 | 0 | 99 | 0 | 100 | 0 | 0 |
| E. amnigenus biogroup I' | 100 | 92 | 0 | 55 | 0 | 70 | 0 | 0 |
| E. asburiae' | 2 | 0 | 0 | 95 | 0 | 100 | 0 | 0 |
| E. hormaechei' | 100 | 52 | 0 | 91 | 0 | 96 | 0 | 0 |
| E. intermedium | 100 | 89 | 0 | 89 | 0 | 65 | 0 | 0 |
| E. dissolvens | 100 | 0 | 0 | 100 | 0 | 100 | 0 | 0 |
| E. nimipressuralis | 100 | 0 | 0 | 100 | 0 | 0 | 0 | 0 |

FIG. 4

Percent Strains Matching Multitest Screening Criteria for Group 1

| Group 1 | Initial Screen VP⁻ Mot⁻ H$_2$S⁻ % Original | Screen 1 LDC⁻ Ind⁻ Cit⁺ | | Screen 1a LDC⁻ Ind⁻ Cit⁺ODC⁺ | | Screen 1b LDC⁻ Ind⁻ Cit⁺Ado⁻ | | Screen 2 YP⁺ | |
|---|---|---|---|---|---|---|---|---|---|
| | | % Original | % Initial | % Original | % Initial | % Original | % Initial | % Original | % Initial |
| K. ornithinolytica' | 30 | 0 | 0 | 0 | 0 | 0 | 0 | 0 | 0 |
| K. ozaenae' | 100 | 18 | 18 | 0.1 | 0.1 | 0.5 | 0.5 | 0 | 0 |
| K. rhinoscleromatis' | 100 | 0 | 0 | 0 | 0 | 0 | 0 | 0 | 0 |
| Citrobacter sp. 9' | 100 | 0 | 0 | 0 | 0 | 0 | 0 | 0 | 0 |
| Citrobacter sp. 10' | 10.89 | 3.6 | 33 | 0 | 0 | 3.6 | 33 | 0 | 0 |
| E. aerogenes' | 0.06 | 0.001 | 1.9 | 0.00002 | 0.04 | 0.00002 | 0.04 | 0 | 0 |
| E. agglomerans group' | 4.5 | 1.8 | 40 | 0 | 0 | 1.7 | 37 | 3.4 | 75 |
| E. asburiae' | 98 | 98 | 100 | 93.1 | 95 | 98 | 100 | 0 | 0 |

FIG. 5

Percent Strains Matching Multitest Screening Criteria for Group 2

| Group 2 | Initial Screen VP⁻ Mot⁺H₂S⁻ % Original | Screen 1 YP⁺ % Original | Screen 1 YP⁺ % Initial | Screen 1a LDC⁻ ADH⁻ Ind⁻ ODC⁻ % Original | Screen 1a LDC⁻ ADH⁻ Ind⁻ ODC⁻ % Initial | Screen 2 LDC⁺ % Original | Screen 2 LDC⁺ % Initial |
|---|---|---|---|---|---|---|---|
| C. freundii' | 19.6 | 0 | 0 | 4.3 | 22 | 0 | 0 |
| C. diversus (koseri)' | 95 | 0 | 0 | 0.002 | 0 | 0 | 0 |
| C. amalonaticus' | 90.25 | 0 | 0 | 0 | 0 | 0 | 0 |
| C. farmeri' | 97 | 0 | 0 | 0 | 0 | 0 | 0 |
| C. youngae' | 33.3 | 0 | 0 | 13.4 | 40 | 0 | 0 |
| C. braakii' | 34.8 | 0 | 0 | 0.5 | 1.5 | 0 | 0.0 |
| C. sedlakii' | 100 | 0 | 0 | 0 | 0 | 0 | 0 |
| Citrobacter sp. 10' | 22.1 | 0 | 0 | 14.8 | 67 | 0 | 0 |
| Citrobacter sp. 11' | 33 | 0 | 0 | 0 | 0 | 0 | 0 |
| E. aerogenes' | 1.94 | 0 | 0 | 0.001 | 0 | 1.90 | 98 |
| E. agglomerans group' | 25.5 | 19.1 | 75 | 20.4 | 80 | 0 | 0 |

FIG. 6

Percent Strains Matching Multitest Screening Criteria for Group 3

| Group 3 | Initial Screen VP$^+$Mot$^-$H$_2$S$^-$ % Original | Screen 1 LDC$^-$ % Original | Screen 1 LDC$^-$ % Initial | Screen 2 LDC$^+$ODC$^+$Ind$^-$ % Original | Screen 2 LDC$^+$ODC$^+$Ind$^-$ % Initial |
|---|---|---|---|---|---|
| K. pneumoniae' | 98 | 1.96 | 2 | 0 | 0 |
| K. oxytoca' | 95 | 0.95 | 1 | 0 | 0 |
| K. ornithinolytica' | 70 | 0 | 0 | 0 | 0 |
| K. planticola' | 98 | 0 | 0 | 0 | 0 |
| K. terrigena | 100 | 0 | 0 | 20 | 20 |
| E. aerogenes' | 2.94 | 0.06 | 2 | 2.82 | 96 |
| E. cloacae' | 5 | 5 | 100 | 0 | 0 |
| E. agglomerans group' | 10.5 | 10.5 | 100 | 0 | 0 |
| E. gergoviae' | 10 | 1 | 10 | 9 | 90 |
| E. sakazakii' | 4 | 4 | 100 | 0 | 0 |
| E. taylorae' | 1 | 1 | 100 | 0 | 0 |
| E. amnigenus biogroup I' | 8 | 8 | 100 | 0 | 0 |
| E. asburiae' | 2 | 2 | 100 | 0 | 0 |
| E. hormaechei' | 48 | 48 | 100 | 0 | 0 |
| E. intermedium | 11 | 11 | 100 | 0 | 0 |
| E. dissolvens | 100 | 100 | 100 | 0 | 0 |
| E. nimipressuralis | 100 | 100 | 100 | 0 | 0 |

FIG. 7

***Enterobacter* spp. Presumptive Identification Flowchart**

METHOD FOR *ENTEROBACTER* IDENTIFICATION

RELATED APPLICATION

This application does not claim the benefit of priority from a U.S. Provisional application.

FIELD OF THE INVENTION

The present invention is generally related to products and methods permitting the identification of *Enterobacter* species organisms.

BACKGROUND OF THE INVENTION

*Enterobacter* spp. are Gram-negative, rod-shaped, motile, nonsporeforming bacteria having nonmotile exceptions such as *E. asburiae, E. dissolvens, E. nimipressuralis* and *E. hormaechei*. Some of the species, such as *E. sakazakii* have been found in powdered milk products and have been associated with high infant fatality rates. *Enterobacter*, particularly *Enterobacter cloacae* and *Enterobacter aerogenes*, are important nosocomial pathogens responsible for a variety of infections, including bacteremia, lower respiratory tract infections, skin and soft tissue infections, urinary tract infections (UTIs), endocarditis, intra-abdominal infections, septic arthritis, osteomyelitis, and ophthalmic infections. Among the predisposing factors for such bacterial infections by humans are prolonged hospitalization, in particular in an intensive care unit (ICU); prior treatment with antibiotics; general debilitation; and immunosuppression.

The treatment of *Enterobacter* is complicated by the fact that multiple strains have antibiotic resistances. These bacteria possess inducible beta-lactamases, which are undetectable in vitro but are also responsible for resistance during treatment. Physicians treating patients infected with these bacteria are well advised to avoid certain antibiotics, such as third-generation cephalosporins, because resistant mutants can quickly appear. The crucial first step of treating an infected patient is appropriate identification of the bacteria. However, problems associated with identification occur. The clinical presentation of the various *Enterobacter* infections is not specific enough to permit clinical differentiation from that of other bacterial infections, such as *Klebsiella* and *Citrobacter*. Such *Enterobacter* identification is further complicated by the fact that strains of the *Enterobacter* species are genetically and phenotypically heterogeneous making it difficult to develop a test that would identify all strains.

SUMMARY OF THE INVENTION

Accordingly, it is an object of the present invention to meet the foregoing needs of *Enterobacter* identification by providing products and methods that differentiate *Enterobacter* from other bacteria, such as, but not limited, to *Klebsiella* and *Citrobacter*.

One embodiment of the present invention is a method of identifying *Enterobacter*, comprising the steps of: a) obtaining a sample to be tested from a source (such as drinking water) where contamination is suspected; b) incubating a first portion of the sample with a first CHRO agar or incubating the first portion of the sample with a XLD agar, selecting one or more mucoid yellow colonies without black centers, applying a portion of each of the mucoid yellow colonies without black centers on a second CHRO agar and incubating the second CHRO agar; c) isolating one or more cultures having metallic medium-to-dark-blue or purple-blue colonies on the first or second CHRO agar; d) incubating a portion of each of the one or more cultures having metallic medium-to-dark-blue or purple-blue colonies separately on TSI agar; e) selecting one or more cultures growing on the TSI agar, wherein the one or more cultures growing on the TSI agar results in the TSI agar having a yellow (acidic) butt without blackening ($H_2S$-negative); f) incubating a portion of each of these one or more cultures growing on the TSI agar separately with each of the materials selected from the group consisting of VP and Mot; g) characterizing the phenotype of the one or more cultures as being a $VP^+Mot^+H_2S^-$, thereby presumptively identifying the one or more suspect *Enterobacter* culture as each being a strain of *Enterobacter*. The method may include the step of transferring the sample from the source of contamination to a laboratory for testing, that is, if the testing at the site is not possible or convenient.

Another embodiment of the present invention is a method of identifying *Enterobacter*, comprising the steps of: a) obtaining a sample to be tested from a source (such as drinking water) where contamination is suspected; b) incubating a first portion of the sample with a first CHRO agar or incubating the first portion of the sample with a XLD agar, selecting one or more mucoid yellow colonies without black centers, applying a portion of each of the mucoid yellow colonies without black centers on a second CHRO agar and incubating the second CHRO agar; c) isolating one or more cultures having metallic medium-to-dark-blue or purple-blue colonies on the first or second CHRO agar; d) incubating a portion of each of the one or more cultures having metallic medium-to-dark-blue or purple-blue colonies separately on TSI agar; e) selecting one or more cultures growing on the TSI agar, wherein the one or more first cultures growing on the TSI agar result in the TSI agar having a yellow (acidic) butt without blackening ($H_2S$-negative); f) incubating a portion of the one or more cultures growing on the TSI agar, separately with each of the materials selected from the group consisting of VP, and Mot; g) isolating one or more $VP^-Mot^-H_2S^-$ culture; h) incubating an aliquot of each of the one or more $VP^-Mot^-H_2S^-$ cultures separately with one or more of the materials selected from the group consisting of LDC, IND, CIT, ADO and YP; i) characterizing the phenotype of the one or more suspect *Enterobacter* culture as being $VP^-Mot^-H_2S^-LDC^-Ind^-Cit^+Ado^-$, or $VP^-Mot^-H_2S^-LDC^-Ind^-Cit^+ODC^+$, or $VP^-Mot^-H_2S^-YP^+$, thereby presumptively identifying the suspect *Enterobacter* cultures as each being a strain of *Enterobacter*. This method may include the additional step of transferring the sample from the source of contamination to a laboratory for testing if testing at the site is not possible or convenient.

Another embodiment of the present invention includes a method of identifying *Enterobacter*, including the steps of: a) obtaining a sample to be tested from a source (such as drinking water) where contamination is suspected; b) incubating a first portion of the sample with a first CHRO agar or incubating the first portion of the sample with a XLD agar, selecting one or more mucoid yellow colonies without black centers, applying a portion of each of the mucoid yellow colonies without black centers on a second CHRO agar and incubating the second CHRO agar; c) isolating one or more cultures having metallic medium-to-dark-blue or purple-blue colonies on the first or second CHRO agar; d) incubating a portion of each of the one or more cultures having metallic medium-to-dark-blue or purple-blue colonies separately on TSI agar; e) selecting one or more cultures growing on the TSI agar, wherein the one or more cultures growing on the TSI agar result in the TSI agar having a yellow (acidic) butt without blackening (H$_2$S-negative); f) incubating a portion of each of the one or more cultures growing on the TSI agar separately with each of the materials selected from the group consisting of VP and Mot; g) isolating one or more VP$^-$Mot$^+$H$_2$S$^-$ cultures; h) incubating a portion of each of the one or more VP$^-$Mot$^+$H$_2$S$^-$ cultures separately with each material selected from the group consisting of YP and LDC; and i) characterizing the phenotype of the suspect *Enterobacter* culture as being VP$^-$Mot$^+$H$_2$S$^-$YP$^+$; or VP$^-$Mot$^+$H$_2$S$^-$LDC$^+$; thereby presumptively identifying the one or more suspect *Enterobacter* cultures as each being a strain of *Enterobacter*. This method may include the additional step of transferring the sample from the source of contamination to a laboratory for testing if testing at the site is not possible or convenient.

Another embodiment of the present invention includes a method of identifying *Enterobacter*, including the steps of: a) obtaining a sample to be tested from a source (such as drinking water) where contamination is suspected; b) incubating a first portion of the sample with a first CHRO agar or incubating the first portion of the sample with a XLD agar, selecting one or more mucoid yellow colonies without black centers, applying a portion of each of the mucoid yellow colonies without black centers on a second CHRO agar and incubating the second CHRO agar; c) isolating one or more cultures having metallic medium-to-dark-blue or purple-blue colonies on the first or second CHRO agar; d) incubating a portion of each of the one or more cultures having metallic medium-to-dark-blue or purple-blue separately on a TSI agar; e) selecting one or more cultures growing on the TSI agar, wherein the one or more cultures growing on the TSI agar result in the TSI agar having a yellow (acidic) butt without blackening (H$_2$S-negative); f) incubating an aliquot of each of the one or more cultures growing on the TSI agar separately with each of the materials selected from the group consisting of VP and Mot; g) isolating one or more VP$^+$Mot$^-$H$_2$S$^-$ cultures; h) incubating a portion of the one or more VP$^+$Mot$^-$H$_2$S$^-$ cultures separately with each of the materials selected from the group consisting of LDC, ODC, and IND; i) characterizing the phenotype of the suspect *Enterobacter* culture as being VP$^+$Mot$^-$H$_2$S$^-$LDC$^-$; or VP$^+$Mot$^-$H$_2$S$^-$LDC$^+$ODC$^+$Ind$^-$; thereby presumptively identifying the one or more suspect *Enterobacter* cultures as each being a strain of *Enterobacter*. This method may include the additional step of transferring the sample from the source of contamination to a laboratory for testing if testing at the site is not possible or convenient.

Another embodiment of the present invention includes a kit for detecting the *Enterobacter* in a sample suspected of bacterial contamination, comprising: a) a device for collecting a sample; b) a first container holding a CHRO agar, a second container holding TSI agar, a third container holding container holding Mot medium; and c) a device for transferring a portion of the sample to each of the containers; wherein the contents of the containers undergo a visible detectable change as a result of the growth of a bacterial contamination; thereby presumptively identifying a strain of *Enterobacter*. A kit of the present invention may further comprise a container holding XLD agar. A kit of the present invention may further comprise one or more of the containers selected from the group consisting of: a container holding VP broth, a container holding testing solution 1 for the VP test, a container holding testing solution 2 for the VP test, a container holding XLD agar, a container holding CIT agar, a container holding materials for the ADO test, a container holding materials for the IND test, a container holding materials for the LDC test, and container holding materials for the ODC test.

BRIEF DESCRIPTION OF THE DRAWINGS

The accompanying drawings, which are incorporated in and constitute a part of this specification, illustrate embodiments of the present invention and, together with the description, explain the advantages and principles of the invention.

FIG. 1 illustrates the biological/microbiological tests and differential materials chosen by the inventor to develop the methods of the present invention. XLD (Xylose Lysine Desoxycholate agar), CHRO(CHROMagar Orientation agar), TSI (Triple Sugar Iron agar), VP (Voges-Proskauer Test), Mot (Motility Test), LDC (Lysine Decarboxylase Broth), ODC (Ornithine Decarboxylase Broth), IND (Indole Test), CIT (Simmons Citrate Agar)

FIG. 2 illustrates microbiological and biochemical characteristics of *Klebsiella, Citrobacter*, and *Enterobacter* species. The tests are defined as observed in FIG. 1, for example, VP means the Voges-Proskauer Test.

FIG. 3 illustrates the placement of strains into Four Groups based on VP, Mot and TSI test results and statistical analysis using Formulae (1). The tests are defined as observed in FIG. 1, for example, VP means the Voges-Proskauer Test.

FIG. 4 illustrates microbiological and biochemical characteristics of *Klebsiella, Citrobacter*, and *Enterobacter* Species for strains placed in the four groups. The tests are defined as observed in FIG. 1, for example, VP means the Voges-Proskauer Test.

FIG. 5 illustrates the placement of Group 1 strains into Groups based on LDC, IND, CIT, ODC, ADO, and YP (yellow pigment production observation) test results and statistical analysis using Formulae (2). The groups are called Screen 1, Screen 1a, Screen 1b, and screen 2.

FIG. 6 illustrates the placement of Group 2 strains into Groups based on YP, LDC, ADH, IND, and ODC test results and statistical analysis using Formulae (2). The groups are called Screen 1, Screen 1a, and Screen 2.

FIG. 7 illustrates the placement of Group 3 strains into Groups based on LDC, ODC and IND test results and statistical analysis using Formulae (2). The groups are called Screen 1 and Screen 2.

DETAILED DESCRIPTION OF THE INVENTION

Figure 8:
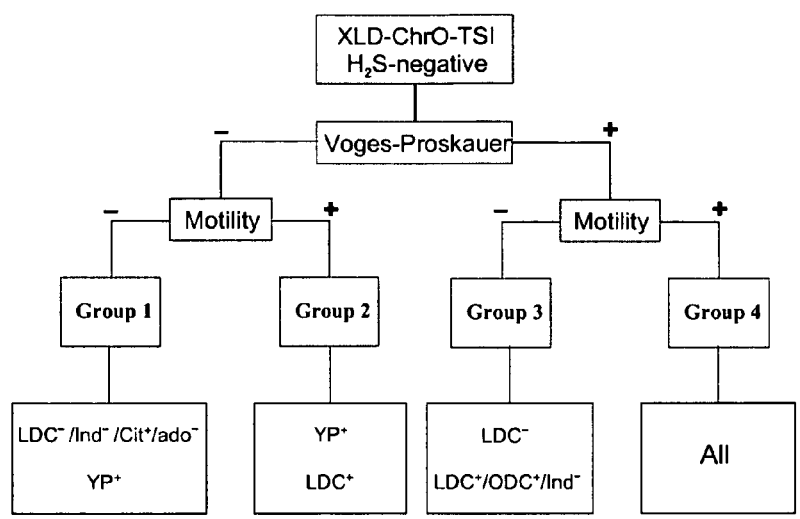
FIG. 8 is a flow chart of the steps of the methods of the present invention enabling the identification of strains of *Enterobacter*.

Reference will now be made to preferred embodiments of this invention, examples of which will be obvious from the description of the invention. Terms have been defined for purposes of further describing the invention.

The term "ADO" means adonitol fermentation test. In this case, the organism is grown in a medium containing peptone, phenol red, and adonitol. If the organism metabolizes adonitol, subsequent acid production will result in lowered pH and medium will become yellow and the organism is characterized as being Ado$^+$. However, if the organism is unable to ferment adonitol, it will result in a pink or red medium and the organism is characterized as being Ado$^-$.

The term "XLD" means a Xylose Lysine Desoxycholate (XLD) agar. Cultures growing on XLD agar and producing mucoid, yellow colonies are further tested to find out if they are *Enterobacter* (suspect *Enterobacter* cultures). Rest of the colonies is presumed not to belong to the *Enterobacter* genus.

The term "CHRO" means a CHROMagar Orientation (CHRO) agar as described in the specification. Cultures growing on CHRO agar and producing medium to dark metallic blue colonies are further tested to find out if they are *Enterobacter* (suspect *Enterobacter* cultures). Rest of the colonies is presumed not to belong to the *Enterobacter* genus.

The term "CIT" means Simmons Citrate (CIT) test as described in the specification. A culture able to grow on CIT Agar is characterized as being Cit$^+$. A culture unable to grow on CIT Agar, or having a growth no larger than a pinpoint, is characterized as being Cit$^-$.

The term "culture" means bacteria grown for scientific purposes.

The term "IND" means an Indole (IND or Ind) test as described in the specification. A culture growing on Tryptone water and upon mixing with Kovac's Indole reagent that results in a bright pink color is characterized as being Ind$^+$. A culture growing on Tryptone water and mixed with Kovac's Indole reagent that does not result in a bright pink color is characterized as being Ind$^-$.

The term "infection" means an act or process of infecting; also: the establishment of a pathogen in its host after invasion.

The term "inoculated" means a method of transferring a sample, organism, or other material from one material to another. Such transfer may occur by stab, loop, dropper, swab, pipette, etc.

The term "LDC" means a Lysine Decarboxylase (LDC) test as described in the specification. A culture growing on LDC broth that turns the broth turbid-purple to faded-yellow-purple color is characterized as being LDC$^+$. A culture growing on LDC broth that does not turn the broth turbid-purple to faded-yellow-purple color, but remains turbid or clear, bright yellow color is characterized as being LDC$^-$.

The term "Mot" means a Motility (Mot) test as described in the specification. A culture that grows on motility medium specifically in the region where it was applied is characterized as being Mot$^-$. A culture that grows on motility medium by spreading out from where it was applied is characterized as being Mot$^+$.

The term "ODC" means an Ornithine Decarboxylase (ODC) test as described in the specification. A culture that grows on ODC broth that turns the broth turbid-purple to faded-yellow-purple color is characterized as being ODC$^+$. A culture that grows on ODC broth that does not turn the broth turbid-purple to faded-yellow-purple color, but remains turbid or clear, bright yellow color is characterized as being ODC$^-$.

The term "suspect *Enterobacter* culture" means a mucoid yellow culture grown on Xylose Lysine Desoxycholate (XLD) Agar. Alternatively, a suspect *Enterobacter* culture means a medium to dark blue culture grown on CHROMagar orientation (CHRO) Agar.

The term "TSI" means a Triple Sugar Iron (TSI) agar as described in the specification. A culture that grows on a TSI agar slant that results in a non-blackening of the butt of the tube is characterized as being $H_2S$-negative ($H_2S^-$). A culture that grows on a TSI agar slant that results in a blackening of the butt of the tube is characterized as $H_2S$-positive ($H_2S^+$). The agar is also observed for acid (yellow) or alkaline (red) color production both in butt and slant. Therefore, the observation results are recorded as "A" for acid, "K" for alkaline, "+" for $H_2S$-positive ($H_2S+$ or TSI$^+$), and "−" for $H_2S$-negative ($H_2S^-$ or TSI$^-$). The recording is in the following order Slant/Butt/$H_2S$. For example, yellow (acid) butt, red (alkaline) slant, and no blackening (i.e. no $H_2S$ production) will be recorded as "K/A/−".

The term "VP" means a Voges-Proskauer (VP) test as described in the specification. A culture that grows on VP broth but does not cause the VP broth to change a color or change its color to a copper hue is characterized as being VP$^-$. A culture that grows on VP broth resulting in the VP broth turning a red, or an eosin pink color, is characterized as being VP$^+$.

The term "YP" means yellow pigment production observation. Colonies grown on a standard microbiological agar are observed for yellow pigment production and the culture producing yellow-pigmented colonies is characterized as being YP$^+$. The culture that fails to produce yellow-pigmented colonies is characterized as being YP$^-$. Trypticase Soy agar (TSA) is generally the agar used for this test. However, other media including Motility Test Medium described here can be used for simultaneous observation of the yellow pigmentation and motility.

Several commercial brands of TSA agar are available and may be used in the present invention. Alternatively, TSA agar may be made from the following materials. 15 grams Pancreatic Digest of Casein, 5 grams Papaic Digest of Soybean Meal, 5 grams NaCl, 15 grams Agar, 1 liter distilled water. Heat with agitation to dissolve agar. Boil 1 min. Dispense into tubes or Petri dishes. Autoclave for 15 min at 121° C. Final pH, 7.3±0.2)

A new technique for detecting *Enterobacter* contamination in a sample such as a liquid has been discovered. This technique is useful for any application in which it is necessary to monitor the biological contamination level, for example drinking water, recreational waters, food processing waters, and medical laboratories. The sample is placed in contact with multiple differentiating materials to identify cultures having phenotypes that are indicative of *Enterobacter*.

Sample Collection

Samples are collected as described in the USEPA microbiology methods manual, Section II, A. The present invention may be used on a sample at its location, or alternatively, a sample maybe transported to a test site, using insulated containers able to maintain a storage temperature of 1-4° C. during transit. It is preferred that the samples are not held longer than 6 hours prior to the initiation of analyses. Samples used in the present invention include, but are not limited, to materials such as blood, water, soil, foods (such as vegetables), plants, and sewage.

Microbiological and Biochemical Tests and Differential Materials

Microbiological and biochemical tests and differential materials are used in the present invention to identify *Enterobacter* within a sample suspected of contamination.

A test used in the present invention involves Xylose Lysine Desoxycholate (XLD) Agar that is commercially available. XLD agar may also be prepared from the following materials: 3 grams Yeast extract, 5 grams L-lysine, 3.75 g Xylose, 7.5 grams Lactose, 7.5 grams Sucrose, 2.5 grams Sodium Desoxycholate, 0.8 g Ferric Ammonium Citrate, 6.8 grams Sodium Thiosulfate, 5 grams NaCl, 15 grams Agar, 0.8 grams Phenol Red, 1 liter of distilled water. If the XLD agar is prepared from these materials, the materials are combined and mixed well to form a solution having a final pH of 7.4±0.2. The solution is heated with agitation just enough to begin boiling, then autoclaved for 15 minutes at standard temperature and pressure (STD T&P, 121° C. 15 psi) then cooled to 45-50° C., and poured into 20 ml portions into sterile 15×100 mm Petri dishes. The XLD plates are dried on a level surface at room temperature with lids closed. After the agar solidifies, the plates are inverted and allowed to dry thoroughly with covers partially removed. Once the plates are dried the covers are placed over the plates. It is preferred that the drying takes place in a bio-safety cabinet with sterile-air laminar flow and that the XLD plates are not stored more than 1 day prior to use. If a gram-negative bacterium ferments lactose and/or sucrose, acid end products are then produced and cause the cultures and the phenol red in the agar around the cultures to turn yellow. If lactose and sucrose are not fermented but the amino acid lysine is decarboxylated to form ammonia, this alkaline end product will cause the phenol red in the agar around the cultures to turn a deeper red. Sometimes the sugars are fermented producing acid end products and lysine is broken down producing alkaline end products. In this case, some of the culture and part of the agar turns yellow and some of the culture and part of the agar turns a deeper red. If a culture produces hydrogen sulfide, part or the entire colony will appear black, resulting from a thiosulfate reduction. Suspect *Enterobacter* spp. cultures are identified as mucoid, yellow colonies without blackening when grown on Xylose Lysine Desoxycholate Agar (XLD).

Another test used in the present invention is CHROMagar Orientation (CHRO) agar, which is commercially available. Alternatively, CHRO plates may be prepared as per manufacturers recommendation (BD Diagnostics Systems) using the following materials: 16.1 grams of chromopeptone, 1.3 grams chromogen Mix, 15.0 g Agar, 1 liter of distilled water. It is preferred that the plates of CHRO agar surface are smooth and moist, without excessive moisture, and are at room temperature prior to inoculation. After applying a sample to the plates, the plates are incubated aerobically at 35±2° C. for not less than 20 to 24 h in an inverted position (agar-side up). CHRO is a differential material containing artificial substrates (chromogens), which upon degradation will release different colored compounds. Suspect *Enterobacter* cultures are identified as medium to dark metallic blue colonies growing on CHRO Agar.

Another differential selective material used in the present invention is Motility Test Medium. Several commercial brands are available and may be used in the present invention. Alternatively, Motility Test Medium may be made from the following materials: 3.0 grams Beef extract, 10.0 grams Peptone, 5.0 grams NaCl, 4.0 grams Agar, and 1 liter of distilled water. If the Motility Test Medium is made from these materials, the materials are mixed together and heated with agitation to dissolve the agar to form a solution. The solution is dispensed in 100-milliliter portions into 170 milliliter bottles, autoclaved for 15 min at 121° C., and then cooled to 50° C. The final pH of the solution is 7.4±0.2. The cooled solution is aseptically dispensed into 2-milliliter portions into sterile 13×100 mm tubes and is preferably stored at room temperature for two days before use. A tube of Motility Test Medium is inoculated with a culture using a straight wire. The straight wire containing the suspect *Enterobacter* culture is stabbed into the center of the Motility Test Medium. If the culture is motility positive, $Mot^+$, it will spread throughout the medium from the stab. If the culture is motility negative, $Mot^-$, bacteria will only grow where it was stabbed into the medium.

Another differential and selective media used in the present invention is Triple Sugar Iron (TSI) Agar. There are two types of TSI agar that may be used in the present invention. Each type of TSI agar is available commercially, typically as TSI slants. Alternatively, each type of TSI agar may be prepared. For example, the first TSI agar may be prepared from the following materials: 20 grams Polypeptone; 5 grams NaCl; 10 grams Lactose, 10 g Sucrose, 1 gram Glucose, 0.2 g $Fe(NH_4)_2(SO_4)_2 \cdot 6H_2O$, 0.2 g $Na_2S_2O_3$, 0.025 grams Phenol Red, 13 grams Agar, and 1 liter of Distilled Water. If the first TSI agar is made from these materials, the materials are combined and mixed thoroughly, heated with occasional agitation, and then boiled for approximately 1 min to dissolve the materials into a solution. The solution is then placed into 16×150 mm tubes so that they are ⅓ full. The tubes are capped, or plugged, to maintain aerobic conditions, then autoclaved for 15 min at 118° C. Before the media solidifies, incline tubes to obtain 4-5 cm slant and 2-3 cm butt. The final pH of the first TSI agar should be 7.3±0.2. The second TSI may be prepared from the following materials: 3 grams Beef Extract, 3 grams Yeast, 15 grams Peptone, 5 grams Proteose peptone, 1 gram Glucose, 10 grams Lactose, 10 grams Sucrose, 0.2 grams FeSO, 5 grams NaCl, 0.3 grams $Na_2S_2O_3$, 0.024 grams Phenol Red, 12 grams Agar, 1 liter distilled water. The preparation of the second media is the same as the first.

As used in the present invention, the TSI Agar is inoculated with suspect *Enterobacter* culture and is incubated, preferably overnight. TSI Agar is a differential material containing protein, lactose, sucrose, glucose, a sulfur source (thiosulfate), an $H_2S$ indicator (ferric ammonium sulfate), and a pH indicator (phenol red which is yellow at pH 6.8 or below and red above it). Specifically, TSI contains ten times as much lactose and sucrose as glucose; consequently, cultures that ferment glucose produce a variety of acids, turning the color of the medium from red to yellow. Larger amounts of acid are produced in the butt of the tube (fermentation) than on the slant (respiration). Organisms growing on the slant also produce alkaline products from the oxidative decarboxylation of peptone. The alkaline products neutralize the small amounts of acids present in the slant but are unable to neutralize the large amounts of acid produced in the butt. Thus the appearance of an alkaline (red) slant and an acid (yellow) butt after 24 hours incubation indicates that the organism is a glucose fermenter but is unable to ferment lactose or sucrose. Bacteria which ferment lactose and/or sucrose, in addition to glucose, produce such large amounts of acid that the oxidative deamination of protein that may occur in the slant does not yield enough alkaline products to cause a reversion of pH in that region. Thus these bacteria produce an acid slant (yellow slant) and acid butt (yellow butt). Gas production, carbon dioxide and hydrogen, is detected by the presence of cracks or bubbles in the medium when gas pockets form. Hydrogen sulfide gas is produced as a result of the reduction of thiosulfate. $H_2S$ is a colorless gas and can be detected by the presence of the indicator, such as ferric ammonium sulfate. $H_2S$ combines with the ferric ions to form ferrous sulfate which is an insoluble black precipitate. Reduction of thiosulfate will occur only in an acid environment therefore the blackening may only be seen in the butt of the tube ($H_2S^+$). A non-blackening of the butt of the tube is indicative of a culture unable to reduce thiosulfate ($H_2S^-$).

A biochemical test used in the present invention is the Voges-Proskauer (VP) Test. Several commercially available brands of VP broth may be used in the present invention. Alternatively, the VP broth is made using the following materials: 7.0 grams Peptone, 5.0 grams Glucose, 5.0 grams Phosphate buffer, and 1 liter of distilled water. If the VP broth is made from such materials, the materials are combined and mixed well, then dispensed in 5 milliliter aliquots into glass tubes having self-sealing screw caps. The tubes are autoclaved at STD T&P for no longer than 10 min (to prevent glucose caramelization), then cooled to room temperature prior to use. The final pH of the VP broth is 6.9±0.2. The VP broth is inoculated with culture and then incubated for 48 hours. Barritt's Reagent A (α-napthol) and Barritt's Reagent B (creatine/potassium hydroxide) are then added to the sample. After gently shaking the tube for aeration, formation of a red or eosin pink color will indicate a positive reaction (VP$^+$). No color change or a copper color is a negative result (VP$^-$). Reagents A and B may be purchased commercially. Alternatively, Reagent A may be made from the following materials: 5 grams of α-Naphthol and 100 milliliters of alcohol (absolute). If Reagent A is made from the materials, the materials are combined before using. Reagent B may be made from the following materials: 0.3 grams of Creatine, 40 grams of Potassium Hydroxide and an amount of distilled water to obtain a final volume of 100 milliliters. If Reagent B is made from the materials, the materials are combined before using. The VP test identifies organisms able to produce acetoin from the degradation of glucose during a 2,3-butanediol fermentation.

Another differential media used in the present invention is the Lysine Decarboxylase (LDC) broth. The broth is prepared by using the following materials: 5.0 grams of Peptic Digest of Animal Tissue, 5.0 grams of Beef Extract, 0.5 grams of Dextrose, 0.005 grams of Pyridoxal, 0.01 grams of Bromcresol Purple, 0.005 grams of Cresol Red, 10.0 grams of L-Lysine. The material is combined and heated until dissolved. Dispense 5 ml portions into 16×125 mm screw-cap tubes. Autoclave loosely capped tubes 15 min at 121° C. Screw the caps on tightly for storage and after inoculation. Final pH, 6.0±0.2. The LDC broth allowed to cool below 37° C. and then inoculated with culture so that the culture is emulsified below the surface of the broth. A control tube that contains no amino acid is also inoculated. All tubes including the control are gently overlaid with 2 to 3-ml (4-mm layer) of sterile mineral oil and incubated in ambient air at 35° C. Tubes are checked daily for up to four days, although prolonged incubation (6 to 10 days) may be required to demonstrate weak reactions due to poor decarboxylase activity. The LDC test identifies the existence of decarboxylase enzymes. Decarboxylation is a reaction which removes the carboxyl group of an amino acid, forming alkaline-reacting amines and carbon dioxide. The LDC broth contains amino acid, lysine, along with the pH indicator, bromcresol purple. The LDC broth is inoculated with culture sealed with mineral oil after inoculation to create anaerobic conditions which promote fermentation. Accumulation of acid end products from fermentation is necessary because decarboxylase enzymes are inducible only in the presence of substrate and acid environment. The decarboxylation of the amino acid by the enzyme then results in alkaline end products. These in turn will cause the pH indicator to turn purple (LDC$^+$), that is the culture contains decarboxylase enzymes. If the inoculums, or culture, does not contain a decarboxylation enzyme the pH indicator will not turn purple (LDC$^-$). Lysine and ornithine are common amino acids which are tested for decarboxylation. The control tubes should not turn purple because the substrates (amino acids) of the decarboxylase enzyme are missing.

Another differential media used in the present invention is a Ornithine Decarboxylase (ODC) broth. The ODC broth is prepared by using the following materials: 5.0 grams of Peptic Digest of Animal Tissue, 5.0 grams of Beef Extract, 0.5 grams of Dextrose, 0.005 grams of Pyridoxal, 0.01 grams of Bromcresol Purple, 0.005 grams of Cresol Red, 10.0 grams of L-Ornithine. The material is combined and heated until dissolved. Dispense 5 ml portions into 16×125 mm screw-cap tubes. Autoclave loosely capped tubes 15 min at 121° C. Screw the caps on tightly for storage and after inoculation. Final pH, 6.0±0.2. The ODC broth allowed to cool below 37° C. and then inoculated with culture so that the culture is emulsified below the surface of the broth. A control tube that contains no amino acid is also inoculated. All tubes including the control are gently overlaid with 2 to 3-ml (4-mm layer) of sterile mineral oil and incubated in ambient air at 35° C. Tubes are checked daily for up to four days, although prolonged incubation (6 to 10 days) may be required to demonstrate weak reactions due to poor decarboxylase activity. The ODC test identifies the existence of decarboxylase enzymes. Decarboxylation is a reaction which removes the carboxyl group of an amino acid, forming alkaline-reacting amines and carbon dioxide. The ODC broth contains amino acid, ornithine, along with the pH indicator, bromcresol purple. The inoculated ODC broth is sealed with mineral oil after inoculation to create anaerobic conditions which promote fermentation. Accumulation of acid end products from fermentation is necessary because decarboxylase enzymes are inducible only in the presence of substrate and acid environment. The decarboxylation of the amino acid by the enzyme then results in alkaline end products. These in turn will cause the pH indicator to turn purple (ODC$^+$), that is the culture contains decarboxylase enzymes. If the inoculums, or culture, does not contain a decarboxylation enzyme the pH indicator will not turn purple (ODC$^-$). The control tube should not turn purple because the substrates (amino acids) of the decarboxylase enzyme are missing.

Arginine, another amino acid test mentioned but not used in this invention, undergoes a different chemical reaction: dihydrolysis. However, the test results are interpreted in the same way as LDC and ODC. The differential media used for this purpose is arginine dihydrolase (ADH) broth which is similar to LDC medium described above, except 10.0 grams of L-arginine is used instead of Lysine. The test is conducted in the same manner as LDC. Some organisms that possess dihydrolase enzymes first hydrolyze Arginine to ornithine, which is then decarboxylated to form putrescine. Formation of these amines increases the pH of the medium, changing the color of the indicator from yellow to purple (ADH$^+$), which means that the culture contains needed enzymes. If the inoculum, or culture, does not contain needed enzymes the pH indicator will not turn purple (ADH$^-$), but remain yellow.

It is preferred that a large inoculum is used in LDC, ODC, and ADH tests in order to shorten the incubation times needed for phenotype observation.

Another differential media used in the present invention is Adonitol fermentation (ADO) test. 10 grams Peptone, 1 gram Beef Extract, 10 grams Adonitol, 5 grams Sodium Chloride, 25 milligrams Phenol Red. The materials are combined and mixed well to form a solution having a final pH of 7.4±0.2. The solution is autoclaved for 15 minutes at 121° C. The medium is inoculated with the culture, incubated at 35±2° C. for 4-48 hours, and periodically observed for growth and color change. Peptone provides the carbon and nitrogen required for good growth of a wide variety of organisms. Sodium chloride maintains the osmotic balance of the medium. Phenol red serves as a pH indicator. If the organism ferments Adonitol then the acid produced during the fermentation turns the medium from red-orange to yellow (Ado$^+$); if the carbohydrate is not fermented (Ado$^-$), the medium remains red or becomes alkaline (darker red).

Another differential media used in the present invention is Kovac's Indole (IND) Reagent, a reagent that is part of an Indole Test. Kovac's Indole Reagent is commercially available or can be prepared by using the following materials: 5 grams p-Dimethylaminobenzaldehyde; 75.0 milliliters of Amyl or Butyl Alcohol; and 25.0 milliliters of concentrated HCl. The Indole Test is performed in a test tube by inoculating Tryptone-Water with a culture. The mixture is incubated aerobically at 37° C. for 48 hours. Upon the completion of the incubation period, 1 milliliter of Kovac's Indole reagent is added to the mixture and the color of the mixture is immediately observed. A bright pink color in the top layer indicates the presence of Indole and the culture is characterized as being Ind$^+$, absence of a bright pink color in the top layer indicates the absence of indole and the culture is characterized as being Ind$^-$. It is preferred that a conventional tube Indole Reaction is used in the present invention. Alternatively, a Spot Indole Test may be used in the present invention.

Another differential media used in the present invention is Simmons Citrate (CIT) Agar. This differential media is commercially available or may be prepared from the following materials: 2.0 grams Sodium Citrate; 5.0 grams NaCl; 1.0 grams $K_2HPO_4$, 1.0 gram $NH_4H_2PO_4$, 0.2 grams $MgSO_4$, 0.08 grams Bromthymol blue, 15.0 grams Agar, 1 liter of distilled Water. If preparing the Simmons Citrate Agar, combine all materials to form a mixture, heat the mixture gently with occasional agitation, then boil the mixture for 1-2 min until agar dissolves to form a solution. Fill 13×100 or 16×150 mm screw-cap tubes with the solution so that the tubes are ⅓ full. Autoclave the tubes containing the solution for 15 min at 121° C. Incline tubes to obtain 4-5 cm slants and 2-3 cm butts and allow the solution to solidify. The final pH of the Simmons Citrate Agar should be 6.9±0.2.

Simmons Citrate Agar detects the ability of certain organisms to utilize citrate as its sole source of carbon. The exact nature of the alkaline reaction produced by the organisms that utilize citrate is poorly understood. It appears that the alkaline reaction most likely occurs when excess $CO_2$ is generated as citrate is cleaved to form oxaloacetate. This by-product is decarboxylated to pyruvic acid and $CO_2$; the excess $CO_2$ combines with sodium and water to form sodium carbonate. In addition, bacteria that utilize citrate can extract nitrogen from the ammonium phosphate incorporated in the medium, resulting in the production of ammonia, which combines with water to form $NH_4OH$. These reactions in combination produce an alkaline pH (greater than 7.6), resulting in a color change in the indicator bromthymol blue from green to blue. A positive result is indicated by culture growth, and does not necessarily have to be accompanied by a color change (Cit$^+$). Pinpoint growth, or absence of culture growth, is considered to be a negative result (Cit$^-$). It is preferred that a small inoculum is used to streak a slant, since a large inoculum may result in a false-positive.

The Identification of *Enterobacter*

The methods of the present invention may begin in one of two ways. A portion of a sample may be applied to CHRO agar and the agar is allowed to incubate. Alternatively, when limiting Gram-positive organism growth is desired, a portion of the sample is applied to XLD agar and the XLD agar is incubated. One or more mucoid yellow colonies without black centers that grow on the XLD agar is selected and a portion of each of the one or more mucoid yellow colonies without black centers is applied to a CHRO agar. The CHRO agar is then allowed to incubate. A suspect *Enterobacter* culture is identified on XLD agar as a mucoid yellow culture, or colony. XLD limits Gram-positive organism growth, whereas CHRO does not. Conversely, XLD cannot differentiate between *Enterobacter* and some other Gram-negative organisms, such as *E. coli*, *Klebsiella*, and *Proteus*. A suspect *Enterobacter* culture identified on CHRO agar is a colony growing on the CHRO agar having the appearance of a metallic medium to dark blue or purple-blue colony. A metallic medium to dark blue or purple-blue colony growing on CHRO agar may be a strain of *Klebsiella*, *Enterobacter*, or *Citrobacter*. Consequently, the identity of the bacteria making up a suspect *Enterobacter* culture is not known and could be a strain of *Klebsiella*, *Enterobacter*, or *Citrobacter*. The methods of the present invention are used to identify the bacteria making up a suspect *Enterobacter* culture.

FIG. 2. is a partial list of the CDC published tables of the microbiological and biochemical characteristics of *Klebsiella*, *Enterobacter*, and *Citrobacter* strains as related to corresponding microbiological and biochemical tests. The tables can be found in their entirety in, "Biochemical Identification of New Species and Biogroups of Enterobacteriaceae Isolated from Clinical Specimens," Farmer J. J. III, Journal of Clinical Microbiology Vol. 21:46-76 (1985), the disclosure of which is hereby incorporated in its entirety. The inventor of the present invention studied these published tables using a statistical method and selected nine tests that, if performed after CHRO alone, or XLD and CHRO selection on a suspect *Enterobacter* culture, in the right combination, would allow the identification of *Enterobacter* and exclude *Klebsiella* and *Citrobacter*. FIG. 1 gives general characteristics of *Enterobacter* spp. However, as is seen on FIG. 2, none of them alone can exclude *Klebsiella* or *Citrobacter* without omitting significant portion of *Enterobacter* as well, nor can any of the general phenotypic characteristics of the last six tests listed on FIG. 3 encompasses the entire *Enterobacter* spp. Therefore, different combinations of nine tests were chosen by the inventor after CHRO alone, or XLD and CHRO selection that would identify suspect *Enterobacter* spp. cultures. FIG. 1 lists seven of the nine tests; the eighth and ninth tests selected by the inventor are the yellow-pigment production (YP) test and Adonitol (ADO) fermentation test that is included in FIG. 4. Several of these nine tests if performed in the right combination on a suspect *Enterobacter* culture after CHRO alone, or XLD and CHRO selection, would identify the suspect *Enterobacter* culture as a strain of *Enterobacter* and not *Klebsiella* nor *Citrobacter*.

A New Combination of Tests and Differential Materials Enabling the Presumptive Identification of *Enterobacter*

In FIG. 2 is the list of microbiological and biochemical test results obtained from the CDC published tables on the phenotypic strain percentages of various species of *Klebsiella*, *Enterobacter*, and *Citrobacter* (KEC). The test results indicate the percentage of strains of each of the bacterial species listed displaying positive phenotypes upon testing. These percentages were placed into Formula (1), which computes the strain distribution percentages of a given species ($P_i$) after the initial screen of Voges-Proskauer (VP), motility (Mot), and $H_2S$ (TSI) test combinations.

$$P_i = 100\left(1 - v - \frac{(-1)^v V}{100}\right)\left(1 - \mu - \frac{(-1)^\mu M}{100}\right)\left(1 - \frac{S}{100}\right) \quad (1)$$

Where V, M, and S are the percentages of positive strains of each species for a given differential test reactions from FIG. 2 for each of the following tests: Voges-Proskauer (VP), motility (Mot), and $H_2S$ (TSI), respectively. Greek letters u and M represent Boolean functions for VP and Mot tests, respectively. These Boolean functions acquire a value of 1 when calculating positive phenotype strains for the appropriate test or 0 (zero) when computing negative phenotype strains. (The formula assumes random distribution of the phenotypic stain percentages given in FIG. 2 for a given species).

According to FIG. 2, all of the strains of the entire *Enterobacter* spp. are $H_2S$-negative. Therefore, once they have been selected from CHRO alone or XLD and CHRO and subsequently for TSI⁻ (H₂S⁻) characteristics, the initial screening can only give four phenotypic groupings of the VP and Mot results for the entire *Enterobacter* spp.: VP⁻Mot⁻, VP⁻Mot⁺, VP⁺Mot⁻, VP⁺Mot⁺. The inventor calculated the percentage distribution into these four groups of the entire KEC species listed in FIG. 2 based on the Formula 1 mathematical analysis, as depicted in FIG. 3. As observed in FIG. 3, Group 4 strains have the phenotype VP⁺, Mot⁺ and can only contain the strains of *Enterobacter* spp. and excluding the strains of *Klebsiella* and *Citrobacter* spp. Consequently, a suspect *Enterobacter* TSI⁻ (H₂S⁻) sample selected from CHRO having a phenotype VP⁺, Mot⁺ is presumptively *Enterobacter*. As shown in FIG. 3, a suspect *Enterobacter* culture having a phenotype of Group 1, Group 2, or Group 3 could be a strain of *Klebsiella, Enterobacter*, or *Citrobacter*. Additional tests on these suspect *Enterobacter* cultures would identify the culture as being *Enterobacter* and excluding *Klebsiella* and *Citrobacter*. In order to identify a phenotype applicable to each Group that would identify *Enterobacter* and exclude *Citrobacter* and *Klebsiella*, FIG. 4 was constructed. FIG. 4 distributes KEC species in Group 1, Group 2, and Group 3 based on FIG. 3 results and gives the phenotypic strain percentages from the CDC published tables. For each of the groups (Group 1, Group 2, and Group 3) the inventor selected different arrays of phenotypic characteristics from FIG. 3 that could serve in differentiating species of *Enterobacter* from *Klebsiella* and *Citrobacter*. For this purpose Formula 2 was developed to compute percentages ($P_s$) of the strains of a given species $$P_s = 100 \prod_{i=1}^{n} \left(1 - \delta(i) - \frac{(-1)^{\delta(i)} D(i)}{100}\right) \quad (2)$$

having phenotypic characteristics based on these test arrays' criteria.

In Formula (2), n is number of tests in the combination, D(i) are the percentages of positive phenotype strains of each species for a given array of phenotypic characteristics from FIGS. 3 and 4, δ(i) represent Boolean functions and acquire a value of 1 when calculating positive-test strains for a particular phenotypic trait or 0 (zero) when computing negative-test strains. (The formula assumes random distribution of the phenotypic stain percentages given in FIG. 4 for a given species).

In FIGS. 5-7, the percentage derived from the Formula 2 is referred as "% original" for a given phenotypic array criteria in numbered Screen columns, whilst "% initial" represents to what the percentage of "% original" is of the total strains of a given species in each group that are represented on FIG. 3 (and again in the "Initial Screen" columns of FIGS. 5-7). Using Formula 2 and the data provided in FIG. 4, the inventor identified specific combination of tests, to perform on a suspect *Enterobacter* culture of each of the groups, i.e., Group 1, Group 2, and Group 3, in order to allow the identification of a strain of *Enterobacter*. Several different arrays of these combinations were examined for each group and final selections were made for each group.

Group 1

As observed in FIG. 3, Group 1 contains three *Enterobacter* spp.: *Enterobacter asburiae* (comprising 98% of the species total) *Enterobacter agglomerans* (comprising 4.5% of the species total), and *Enterobacter aerogenes* (comprising 0.06% of the species total). For a Group 1 suspect *Enterobacter* culture, phenotypic array identification tests include Lysine Decarboxylase (LDC) broth, IND test, and Simmons Citrate Agar (CIT) tests. As observed on FIG. 5 ("Screen 1"), when Group 1 strains are tested on Lysine Decarboxylase (LDC) broth, IND test, and Simmons Citrate Agar (CIT) tests the phenotypic characteristics of the strains allow presumptive identification of strains of *Enterobacter* spp. As shown in "Screen 1" column of FIG. 5, it would include the entire strains of *E. asburiae*, which comprises 98% of the species total, and slightly over third of the 4.5% of *E. agglomerans* strains. However, it would not exclude 18% of *K. ozaenae* stains and 3.6% of *Citrobacter* sp. 10 strains, which also have a LDC⁻Ind⁻Cit⁺ phenotype. The addition of an adonitol fermentation (ADO) test in addition to the Lysine Decarboxylase (LDC) broth, Indole (IND) test, and Simmons Citrate Agar (CIT) would extensively (99.5%) exclude strains of *K. ozaenae*, but would not further affect *Citrobacter* spp. 10 strains (See "Screen 1b" on FIG. 5). That is, a suspect *Enterobacter* culture, more specifically a Group 1 suspect *Enterobacter* culture, having the phenotype LDC⁻Ind⁻Cit⁺Ado⁻ excludes more than 99% of the strains of *Klebsella* and *Citrobacter* and is therefore presumptive of a strain of *Enterobacter*.

If higher stringency of excluding *Citrobacter* spp. 10 strains is desired, an alternative approach identifying a suspect *Enterobacter* culture, specifically a Group 1 suspect *Enterobacter* culture, then a substitution of the ADO test with an ornithine decarboxylase (ODC) test could be employed. A group 1 suspect *Enterobacter* culture having the phenotype LDC⁻Ind⁻Cit⁺ODC⁺ would totally exclude *Citrobacter* sp. 10 strains and nearly all (99.9%) *K. ozaenae*; however it would also exclude 5% of *E. asburiae* (See "Screen 1a" on FIG. 5). Therefore a suspect *Enterobacter* culture, specifically a Group 1 suspect *Enterobacter* culture, having a phenotype of LDC⁻Ind⁻Cit⁺Ado⁻ (or for higher stringency, LDC⁻Ind⁻Cit⁺ODC⁺) is presumptively identified as being a strain of *Enterobacter* spp.

Additionally, visual screening of the group for yellow pigmentation (YP⁺) would yield 75% of *E. agglomerans* of this group, which would be otherwise totally excluded as observed on "Screen 2" of FIG. 5. Although only small percentage of the species (4.5% of the total) are represented in this group, the required additional visual screen is worth the effort, especially, since this screen would be excluding all other species or genera. Therefore, all the YP⁺ strain of this group should be considered being identified as *Enterobacter agglomerans*. Consequently, a suspect *Enterobacter* culture, specifically a Group 1 suspect *Enterobacter* culture, having a phenotype of LDC⁻Ind⁻Cit⁺Ado⁻ or LDC⁻Ind⁻Cit⁺ODC⁺. Additionally, all YP⁺ phenotypes of this group are identified as being *Enterobacter agglomerans*.

Group 2

As observed in FIG. 3, Group 2 contains only strains of *Citrobacter* and *Enterobacter* spp. There are only two *Enterobacter* spp. in this group: *Enterobacter agglomerans* (comprising 25.5% of the species total) and *Enterobacter aerogenes* (comprising 1.94% of the species total). For a Group 2 suspect *Enterobacter* culture, a single phenotypic identification test is found to be most suitable for each of these two species used: the Yellow Pigmentation (YP) test for *Enterobacter agglomerans* and Lysine Decarboxylase (LDC) test for *Enterobacter aerogenes*. As observed on FIG. 6, when yellow pigment producing (YP⁺) strains are selected for Group 2 it would identify 75% *Enterobacter agglomerans* of this group. A separate selection for Lysine Decarboxylase positive (LDC⁺) strains for Group 2 would yield the identification of 98% *Enterobacter aerogenes* of this group.

As observed in FIG. 6, Group 2 strains that are YP⁺ are *E. agglomerans*. Group 2 strains that are LDC⁺ are *E. aerogenes*.

Group 3

As shown in FIG. 3, Group 3 consists of *Enterobacter* and *Klebsiella* strains but not strains of *Citrobacter*. Microbiological and biochemical tests used on Group 3 bacteria include the Lysine Decarboxylase (LDC) test, Ornithine Decarboxylase (ODC) test, and the Indole test. As observed on FIG. 7, Group 3 strains that have LDC⁻ phenotype are presumptively strains of the *Enterobacter* spp. LDC⁻ test for the Group 3 strains identify nearly the entire *Enterobacter* spp. of this group. However, the test will not detect *E. aerogenes* of this group, which has a very few (less than 3%) of its strains represented in this group, and most of the *E. gergoviae* of this group, which has 10% of its strains represented in this group. LDC⁻ test for the Group 3 will successfully exclude nearly all the non-Enterobacter species with the exception of less than 2% of *Klebsiella pneumoniae* and less than 1% of *Klebsiella oxytoca* (See "Screen 1" on FIG. 7).

In order to detect missed *E. aerogenes* and *E. gergoviae* strains of this group that could not be identified by the LDC⁻ selection, a new LDC⁺ODC⁺Ind⁻ phenotypic array of selection could be used. Group 3 strains that are LDC⁺ODC⁺Ind⁻ would include 96% and 90% of *E. aerogenes* and *E. gergoviae* of this group, respectively. However, it should be noted that this selection criteria (LDC⁺ODC⁺Ind⁻), although would successfully exclude all other non-Enterobacter species, nonetheless would be including 20% of the strains of *Klebsiella terrigena* (See "Screen 2" on FIG. 7). Consequently, a suspect *Enterobacter* culture, specifically a Group 3 suspect *Enterobacter* culture, that has phenotypes of either LDC⁻ or LDC⁺ODC⁺Ind⁻, is presumptively a strain of *Enterobacter* spp.

Group 4

As can be seen on FIG. 3, only strains of *Enterobacter* spp. are represented in Group 4 and all strains of *Klebsiella* and *Citrobacter* species are excluded from this group. Therefore, all strains displaying Group 4 phenotype (i.e., $H_2S^-VP^+Mot^+$) are identified as *Enterobacter* spp.

KIT

The differential materials (tests) of the present invention are placed into containers that fit into a carrying device, such as a bag, for transportation to area thought to be contaminated with *Enterobacter*. The sample maybe collected into a first container. Alternatively, the sample may be collected directly from the source of suspected contamination by a carrying device such as a swab, loop, etc. The kit includes a container holding CHRO agar, a container holding TSI agar, a container holding VP broth, a container holding testing solution 1 (Barritt's Reagent A) for the VP test, a container holding testing solution 2 (Barritt's Reagent B) for the VP test, and a container holding Mot medium. The kit may include a one or more of the following containers: a container holding XLD agar, a container holding CIT agar, a container holding materials for the ADO test, a container holding materials for the IND test, a container holding materials for the LDC test, and a container holding materials for the ODC test. A carrying device is used to place sample in contact with one or more of the materials described in the specification and located in the containers. The containers holding the materials may be mixed such as mixing the solutions of the VP test. A sample is placed in contact with the containers holding the materials and the inoculated samples are incubated. After the incubation is completed, the materials in the containers are observed to determine if they have undergone a visible detectable change as a result of the growth of the bacterial contamination. Using the methods of the present invention one is able to make a presumptive identification of *Enterobacter*.

The foregoing description of embodiments of the present invention provides an exemplary illustration and description, but is not intended to be exhaustive or to limit the invention to the precise form disclosed. Modifications and variations are possible in light of the above teachings or may be acquired from practice of the invention.

What is claimed is:

1. A method of identifying *Enterobacter*, comprising the steps of:
   (a) obtaining a sample to be tested from a source where contamination is suspected;
   (b) incubating a portion of the sample with a first CHROMagar Orientation (CHRO) agar; or incubating a portion of the sample with an Xylose Lysine Desoxycholate (XLD) agar, selecting one or more mucoid yellow colonies without black centers from the XLD agar, applying a portion of each of the mucoid yellow colonies without black centers on a second CHRO agar and incubating the second CHRO agar;
   (c) isolating one or more cultures having metallic medium-to-dark-blue or purple-blue colonies on the first or second CHRO agar;
   (d) incubating a portion of each of the one or more cultures having metallic medium-to-dark-blue or purple-blue colonies separately on a Triple Sugar Iron (TSI) agar;
   (e) selecting one or more cultures growing on TSI agar, wherein the one or more cultures growing on TSI agar result in the TSI agar having a yellow (acidic) butt without blackening ($H_2S$-negative);
   (f) incubating a portion of each of these one or more cultures growing on TSI agar separately with each of the materials selected from the group consisting of Voges-Proskauer broth (VP) and Motility medium (Mot); and
   (g) characterizing the phenotype of the one or more cultures as being a $VP^+Mot^+H_2S^-$, thereby identifying the one or more suspect *Enterobacter* culture as each being a strain of *Enterobacter*.

2. The method of claim 1, wherein the source is drinking water.

3. The method of claim 1, including the step of transferring the sample from the source of contamination to a laboratory for testing.

4. The method of claim 1, further comprising the steps of:
   (h) isolating one or more $VP^-Mot^-H_2S^-$ cultures;
   (i) incubating an aliquot of each of the one or more $VP^-Mot^-H_2S^-$ cultures separately with one or more of the materials selected from the group consisting of Lysine Decarboxylase (LDC), Indol (IND), Simmons Citrate (CIT), Adonitol (ADO), Ornithine Decarboxylase (ODC), and Yellow Pigment (YP); and
   (j) characterizing the phenotype of the one or more suspect *Enterobacter* culture as being $VP^-Mot^-H_2S^-LDC^-IND^-CIT^+ADO^-$, $VP^-Mot^-H_2S^-LDC^-IND^-CIT^+ODC^+$, or $VP^-Mot^-H_2S^-YP^+$, thereby identifying the suspect *Enterobacter* cultures as each being a strain of *Enterobacter*.

5. The method of claim 1, further comprising the steps of:
   (h) isolating one or more $VP^-Mot^+H_2S^-$ cultures;
   (i) incubating a portion of each of the one or more $VP^-Mot^+H_2S^-$ cultures separately with each material selected from the group consisting of YP and LDC; and
   (j) characterizing the phenotype of the suspect *Enterobacter* culture as being $VP^-Mot^+H_2S^-YP^+$; or $VP^-Mot^+H_2S^-LDC^+$; thereby identifying the one or more suspect

*Enterobacter* cultures as each being a strain of *Enterobacter*.

6. The method of claim 1, further comprising the steps of:
(h) isolating one or more $VP^+Mot^-H_2S^-$ cultures;
(i) incubating a portion of the one or more $VP^+Mot^-H_2S^-$ cultures separately with each of the materials selected from the group consisting of LDC, ODC, and IND; and (j) characterizing the phenotype of the suspect *Enterobacter* culture as being $VP^+Mot^-H_2S^-LDC^{-1}$; or $VP^+Mot^-H_2S^-LDC^+ODC^+IND^-$; thereby identifying the one or more suspect *Enterobacter* cultures as each being a strain of *Enterobacter*.

* * * * *